United States Patent
Zhang et al.

(10) Patent No.: US 11,452,707 B2
(45) Date of Patent: Sep. 27, 2022

(54) USE OF CANNABIDIOL IN PREPARATION OF DRUGS FOR RESISTING AGAINST INFLUENZA

(71) Applicant: HANYI BIO-TECHNOLOGY COMPANY LTD., Beijing (CN)

(72) Inventors: Ke Zhang, Beijing (CN); Xin Tan, Beijing (CN); Xiangdong Li, Beijing (CN); Zhaohui Yu, Beijing (CN)

(73) Assignee: HANYI BIO-TECHNOLOGY (BEIJING) CO., LTD., Beijing (CN)

( * ) Notice: Subject to any disclaimer, the term of this patent is extended or adjusted under 35 U.S.C. 154(b) by 255 days.

(21) Appl. No.: 16/639,858

(22) PCT Filed: Aug. 31, 2017

(86) PCT No.: PCT/CN2017/099956
§ 371 (c)(1),
(2) Date: Feb. 18, 2020

(87) PCT Pub. No.: WO2019/041239
PCT Pub. Date: Mar. 7, 2019

(65) Prior Publication Data
US 2020/0360336 A1    Nov. 19, 2020

(51) Int. Cl.
*A61K 31/352* (2006.01)
*A61P 31/16* (2006.01)
(Continued)

(52) U.S. Cl.
CPC .......... *A61K 31/352* (2013.01); *A61K 9/0053* (2013.01); *A61K 36/73* (2013.01); *A61P 31/16* (2018.01)

(58) Field of Classification Search
CPC .... A61K 31/352; A61K 9/0053; A61K 36/73; A61K 45/06; A61K 31/05; A61K 31/13; A61K 31/196; A61K 31/215; A61K 31/4045; A61K 31/7012; A61K 31/7056; A61P 31/16; A61P 11/00; A61P 29/00
(Continued)

(56) References Cited

U.S. PATENT DOCUMENTS

2016/0199327 A1*  7/2016  Bannister ............. A61K 9/2013
                                                          514/569

OTHER PUBLICATIONS

Garik, Influenza, Wikipedia,, Jan. 2016, p. 1-19. (Year: 2016).*

* cited by examiner

*Primary Examiner* — Taylor V Oh
(74) *Attorney, Agent, or Firm* — Platinum Intellectual Property LLP

(57) ABSTRACT

The present invention belongs to the field of biomedicine and relates to use of cannabidiol in the preparation of anti-influenza drugs. Specifically, the present invention relates to use of any one of (1) to (3) below in the preparation of drugs for treating or preventing influenza or drugs for relieving an influenza symptom: (1) cannabidiol or a pharmaceutically acceptable salt or ester thereof; (2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials. The cannabidiol can effectively inhibit influenza viruses, and has the potential to prepare or be used as a drug for treating or preventing influenza.

7 Claims, 8 Drawing Sheets
Specification includes a Sequence Listing.

(51) Int. Cl.
*A61K 9/00* (2006.01)
*A61K 36/73* (2006.01)

(58) Field of Classification Search
USPC .......................................................... 514/456
See application file for complete search history.

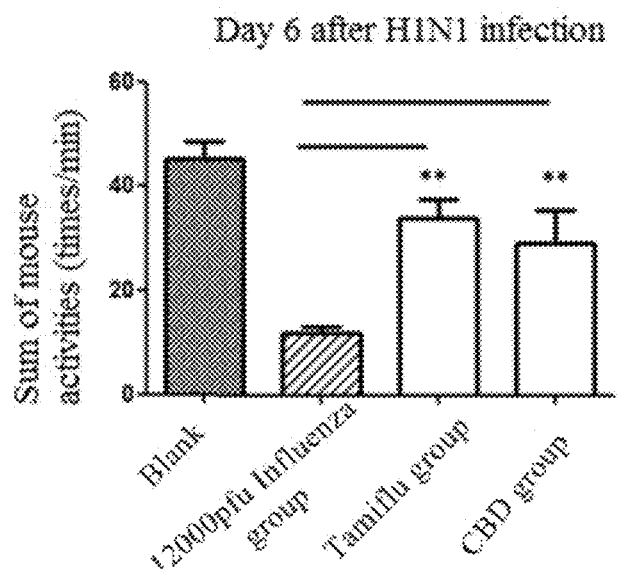
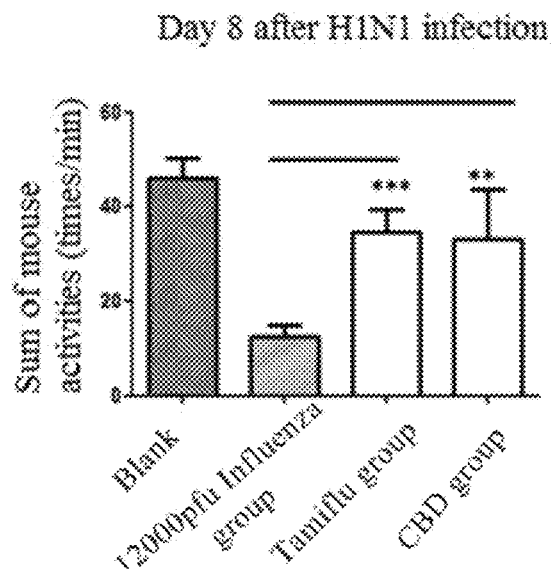
FIG. 3A  FIG. 3B
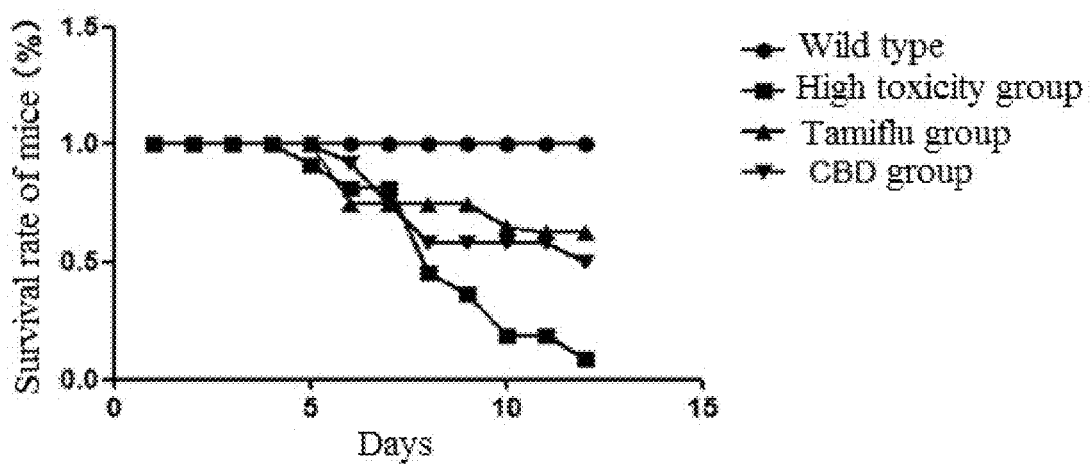
FIG. 4

SEQUENCE LISTING

<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
cggggagtct tcgagctctc                                              20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
ttgtctccga agaaataaga                                              20

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
atggaagatt ttgtgcgaca                                              20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
tgactcgcct tgctcatcga                                              20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
taccggtgcc atagaggtga                                              20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
cgcccctggt aatcctcatc                                              20

<210> SEQ ID NO 7
<211> LENGTH: 20
<212> TYPE: DNA
<213> ORGANISM: Artificial

```
<220> FEATURE:
<223> OTHER INFORMATION: Primer

<400> SEQUENCE: 7
gcgattgaat cccatgcacc                                               20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tccgcgctgg aatactcatc                                               20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
gtggcccata agtcctgctt                                               20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ggtcgctctt tcgaagggaa                                               20

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
gccgcaatat gcacacactt                                               20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
ttgattcgcc tcgttcgtca                                               20

<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
agactaccag ggcagactgt                                               20
```

```
<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
caactggcct ccgatacgaa                                              20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
gcagcaatgg gtctgaggat                                              20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
caatgtttgg aggttgcccg                                              20
```

USE OF CANNABIDIOL IN PREPARATION OF DRUGS FOR RESISTING AGAINST INFLUENZA

RELATED APPLICATIONS

[00001] This application is a United States National Stage Application filed under 35 U.S.C 371 of PCT Patent Application Serial No. PCT/CN2017/099956, filed Aug. 31, 2017, the disclosure of all of which are hereby incorporated by reference in their entirety.

FIELD

The present invention belongs to the field of biomedicine and relates to use of cannabidiol in the preparation of anti-influenza drugs.

BACKGROUND

Influenza (commonly referred to as flu) is an acute respiratory infectious disease caused by influenza virus, which affects humans, birds and livestock. It is a disease that poses a serious threat to human health because of its rapid spread, high morbidity and serious complications.

An influenza virus is an influenza pathogenic factor spread through the acute respiratory tract, and belongs to a single-stranded negative-stranded RNA virus of the Orthomyxovirus family. According to the difference in antigenicity of their nucleoprotein (NP) and matrix protein (M), the influenza viruses can be classified into three types: A, B, and C (Hay et al., 2001). Among them, Influenza A Virus (IAV) is the most common, poses the greatest threat to humans, and may cause seasonal and regional outbreaks of influenza. In addition to infecting people, it can also cause infections in a variety of animals such as birds, pigs and horses.

IAV is a single-stranded negative-stranded 8-segment RNA virus. Each RNA segment is covered with a nucleoprotein (NP) to form ribonucleoproteins (RNPs). The IAV genome encodes at least 13 proteins, PB2, PB1, PB1-F2, N40, PA, PA-X, HA, NP, NA, M 1, M2, NS1 and NS2 respectively. There are 3 proteins distributed on the surface of the IAV envelope, which are HA, NA and M2. The 8 RNA segments of the IAV are all covered with NP. In virions, viral RNA is covered into RNPs by NP and 3 subunits of polymerase, polymerase 1 (PB1), polymerase 2 (PB2), and polymerase A (PA). PB1 functions as an RNA dependent RNA polymerase. PB2 binds to and cleaves the host mRNA cap as a primer to synthesize a viral RNA. PA may function as a host RNA endonuclease and may also have proteolytic activity. NP functions as a single-stranded RNA binding protein and acts as a structural protein in RNPs.

In the IAV genome, genes encoding PA, PB1, PB2, and NP proteins are highly conserved in evolution, and the antigenicity of IAV is highly susceptible to mutation. Therefore, according to the difference in the outer membrane protein hemagglutinin antigen (HA) and neuraminidase (NA) carried, they can be classified into several subtypes. Currently, 16 HA subtypes and 10 NA subtypes have been discovered, which are constantly mutated, arranged and combined to achieve self-evolution, and continue to bring new threats to humans.

Among them, only H1N1, H2N2, and H3N2 mainly infect humans, and natural hosts of many other subtypes are a variety of birds and animals. Among them, H5, H7 and H9 subtype strains are the most harmful to birds. Once the highly pathogenic avian influenza viruses such as H5NI, H7N9 and H9N2 mutate and have human-to-human transmission ability, this will lead to the epidemic of avian influenza among people, indicating that the avian influenza viruses have a great potential threat to humans.

After the IAV enters a cell, its genome needs to be replicated and transcribed by its RNA dependent RNA polymerase (RDRP), and then translated into infectious virus particles. If the polymerase loses activity, the virus cannot be replicated or transcribed to produce an entire virus particle.

Clinical studies have shown that the IAV incubation period is generally 3 to 4 days, up to 7 days. The patient usually presents as fever, cough, and scanty sputum, accompanied by systemic symptoms such as headache, muscle pains, and diarrhea. If the disease is not treated in time, the disease develops rapidly. Severe patients mainly present with acute lung injury (ALI), which may cause serious complications, such as acute pneumonia, bronchitis, congestive heart failure, gastroenteritis, syncope, hallucinations, and the like, and may lead to death in severe cases. ALI refers to pathological features such as pulmonary edema and microatelectasis caused by alveolar capillary damage after severe infection. Acute respiratory distress syndrome (ARDS) is a severe ALI (Bernard et al., 1987), and may also induce systemic inflammatory response syndrome (SIRS). Because the fatality rate of ARDS is as high as 40%-50%, this is also an important reason why IAV will result in death.

At present, the anti-influenza drugs approved by the countries in the world are mainly: an inosine monophosphate dehydrogenase (IMPDH) inhibitor ribavirin, an interferon inducer arbidol hydrochloride, M2 ion channel protein inhibitors amantadine hydrochloride and rimantadine hydrochloride, neuraminidase inhibitors osehamivir phosphate and zanamivir, which are 4 classes and 6 varieties (Glezen, 2006; Kolocouris et al., 1996).

M2 ion channel blockers, including amantadine and rimantadine, prevent virus uncoating by blocking M2 ion channel proteins, such that the viral RNA cannot be released into the cytoplasm, and the early replication of the virus is interrupted, thereby performing an anti-influenza virus function. However, amantadine drugs are not effective against Type B influenza, and they are neurotoxic, and can cause side effects such as insomnia, distraction, and nervousness within hours after taking. Moreover, amantadine drugs easily produce drug-resistant strains under experimental conditions and clinical applications. However, most of the current influenza virus strains have been resistant to these two drugs, and only the influenza A virus has M2 ion channel proteins, so its clinical use is not extensive.

In NA inhibitors, only zanamivir and oseltamivir (Tamiflu) are currently on the market, and another intravenous injection of peramivir was approved in Japan in January 2010. By inhibiting the activity of NA, they prevent sialic acid on the surface of infected cells from being cleaved, resulting in no release of the new virus from the surfaces of the infected cells, thereby preventing the virus from further infecting other cells. However, even with Tamiflu, patients with H5N1 avian influenza have a high mortality, and Tamiflu-resistant virus strains are constantly being isolated. The currently popular IAV has developed resistance to neuraminidase inhibitors. In addition, Tamiflu can cause serious adverse reactions such as sudden breathing difficulties. For example, a study by a Japanese non-profit organization "Pharmacovigilance Center" found that 38 of the 119 deaths who took Tamiflu experienced severe illness or death within 12 hours after taking the drug.

Cannabidiol (CBD) is one of the cannabinoids, and its structural formula is as shown in the following formula I:

formula I

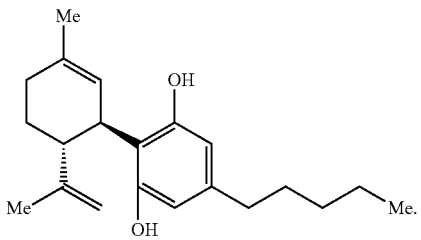

Cannabidiol is extracted from natural plant cannabis, has no mental effect, and has therapeutic effects on anxiety, depression, convulsions and tumors. Studies have shown that CBD has a good anti-inflammatory effect. In 2000, Proceedings of the National Academy of Sciences reported that Dr. M. Feldman of the Kennedy Institute of Rheumatology in London, UK, found that oral and systemic use of CBD can significantly reduce the severity of joint damage and the acute and chronic courses of arthritis. The Immunopharmacol Immunotoxicology in 2015 reported that CBD inhibits LPS-induced acute lung injury (Ribeiro et al., 2015).

Therefore, there is an urgent need to develop new anti-influenza drugs at present.

SUMMARY

After intensive research and creative labor, the inventors have surprisingly found that cannabidiol can effectively inhibit influenza virus and RNA polymerase of the influenza virus, and has the potential to prevent and treat influenza. The following invention is thus provided:

One aspect of the present invention relates to use of any one of (1) to (3) below in the preparation of drugs for treating or preventing influenza or drugs for relieving an influenza symptom:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza is caused by one or more influenza viruses selected from influenza A virus, influenza B virus, and influenza C virus; preferably, the influenza A virus is an influenza A virus of H1N1 subtype, H2N2 subtype, H3N2 subtype, H5NI subtype, H7N9 subtype or H9N2 subtype.

In one embodiment of the present invention, the subject susceptible to the influenza is a mammal (e.g., a human, a simian, a monkey, a pig, a cow or a sheep) or a bird (e.g., a domestic bird such as a chicken, a duck or a goose, or e.g, a wild bird).

In one embodiment of the present invention, the influenza symptom is at least one selected from the following symptoms caused by influenza:

fever, cough, headache, muscle pains, and diarrhea.

In one embodiment of the present invention, the pharmaceutical composition further includes an effective amount of one or more ingredients selected from:

an inosine monophosphate dehydrogenase (IMPDH) inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride;

preferably, the neuraminidase inhibitor is oseltamivir phosphate, oseltamivir (Tamiflu), zanamivir or peramivir.

Another aspect of the present invention relates to use of any one of (1) to (3) below in the preparation of drugs for protecting against an influenza virus (e.g., inhibiting replication of an influenza virus in a host cell):

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza virus is selected from one or more of influenza A virus, influenza B virus, and influenza C virus; preferably, the influenza A virus is an influenza A virus of H1N1 subtype, H2N2 subtype, H3N2 subtype, H5NI subtype, H7N9 subtype or H9N2 subtype.

In one embodiment of the present invention, the host cell is a cell of a mammal (e.g., a human, a simian, a monkey, a pig, a cow or a sheep) or a bird (e.g., a domestic bird such as a chicken, a duck or a goose, or e.g, a wild bird).

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

Still another aspect of the present invention relates to use of any one of (1) to (3) below in the preparation of drugs for inhibiting replication of an influenza virus RNA polymerase, drugs for inhibiting the expression level of an influenza virus RNA polymerase, or drugs for inhibiting the activity of an influenza virus RNA polymerase:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza virus RNA polymerase is selected from one or more of an influenza A virus RNA polymerase, an influenza B virus RNA polymerase, and an influenza C virus RNA polymerase; preferably, the influenza A virus RNA polymerase is an RNA polymerase of an influenza A virus of H1N1 subtype, H2N2 subtype, H3N2 subtype, H5NI subtype, H7N9 subtype or H9N2 subtype.

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

In one embodiment of the present invention, the expression level of the influenza virus RNA polymerase inhibited refers to, for example, a protein level of an influenza virus RNA polymerase or a level of mRNA encoding an influenza virus RNA polymerase.

In one embodiment of the present invention, the expression level of the influenza virus RNA polymerase can be determined by an expression level of any one or more of three subunits PB1, PB2 and PA of the influenza virus RNA polymerase.

Yet another aspect of the present invention relates to a pharmaceutical composition, containing an effective amount of cannabidiol or a pharmaceutically acceptable salt or ester thereof, and one or more pharmaceutically acceptable auxiliary materials.

In one embodiment of the present invention, in the pharmaceutical composition, the cannabidiol is the sole active ingredient. In another embodiment of the present invention, the cannabidiol is used in combination with one or more other known active ingredients for preventing and treating influenza.

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

The pharmaceutical composition may be in the form of any pharmaceutically acceptable dosage form, including: tablets, sugar-coated tablets, film-coated tablets, enteric-coated tablets, capsules, hard capsules, soft capsules, oral liquids, buccals, granules, instant granules, pills, pulvis, pastes, sublimed preparations, suspensions, powders, solutions, injections, suppositories, ointments, plasters, creams, sprays, drops, and patches; preferably oral dosage forms, such as: capsules, tablets, oral liquids, granules, pills, pulvis, sublimed preparations, pastes, and the like. The oral dosage form may contain conventional excipients such as binders, fillers, diluents, tabletting agents, lubricants, disintegrating agents, coloring agents, flavoring agents, and wetting agents, and if necessary, the tablets can be coated. Suitable fillers include cellulose, mannitol, lactose and other similar fillers; suitable disintegrating agents include starch, polyvinylpyrrolidone and starch derivatives, for example, sodium starch glycolate; suitable lubricants include, for example, magnesium stearate. Suitable pharmaceutically acceptable wetting agents include sodium lauryl sulfate.

Preferably, the pharmaceutical composition is an oral preparation.

The dosage of cannabidiol administered to the subject is preferably 0.1-50 mg/kg body weight/day, more preferably 0.5 mg/kg-30 mg/kg body weight/day, 0.5 mg/kg-20 mg/kg body weight/day, 5 mg/kg-30 mg/kg body weight/day or 5 mg/kg-20 mg/kg body weight/day, further preferably 0.5 mg/kg-10 mg/kg body weight/day, particularly preferably 0.5 mg/kg-5 mg/kg body weight/day.

Still yet another aspect of the present invention relates to a combination product, including a product 1 and a product 2 which are individually packaged, wherein, the product 1 is selected from any one of (1) to (3) below:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials;

the product 2 includes an effective amount of one or more ingredients selected from: an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

The present invention further relates to the following aspects:

The present invention relates to a product selected from any one of (1) to (3) below for treating or preventing influenza or relieving an influenza symptom:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza is caused by one or more influenza viruses selected from influenza A virus, influenza B virus, and influenza C virus; preferably, the influenza A virus is an influenza A virus of H1N1 subtype, H2N2 subtype, H3N2 subtype, H5NI subtype, H7N9 subtype or H9N2 subtype.

In one embodiment of the present invention, the subject susceptible to the influenza is a mammal (e.g., a human, a simian, a monkey, a pig, a cow or a sheep) or a bird (e.g., a domestic bird such as a chicken, a duck or a goose, or e.g, a wild bird).

In one embodiment of the present invention, the influenza symptom is at least one selected from the following symptoms caused by influenza:

fever, cough, headache, muscle pains, and diarrhea.

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

The present invention further relates to a product selected from any one of (1) to (3) below for protecting against an influenza virus (e.g., inhibiting replication of an influenza virus in a host cell):

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza virus is selected from one or more of influenza A virus, influenza B virus, and influenza C virus; preferably, the influenza A virus is an influenza A virus of H1N1 subtype, H2N2 subtype, H3N2 subtype, H5NI subtype, H7N9 subtype or H9N2 subtype.

In one embodiment of the present invention, the host cell is a cell of a mammal (e.g., a human, a simian, a monkey, a pig, a cow or a sheep) or a bird (e.g., a domestic bird such as a chicken, a duck or a goose, or e.g, a wild bird).

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

The present invention further relates to a product selected from any one of (1) to (3) below for inhibiting replication of an influenza virus RNA polymerase, inhibiting the expression level of an influenza virus RNA polymerase or inhibiting the activity of an influenza virus RNA polymerase:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza virus RNA polymerase is selected from one or more of an influenza A virus RNA polymerase, an influenza B virus RNA polymerase, and an influenza C virus RNA polymerase; preferably, the influenza A virus RNA polymerase is an RNA polymerase of an influenza A virus of H1N1 subtype, H2N2 subtype, H3N2 subtype, H5NI subtype, H7N9 subtype or H9N2 subtype.

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

The present invention further relates to a method of treating or preventing influenza or relieving an influenza symptom, including a step of administering an effective amount of a product selected from any one of (1) to (3) below to a subject in need:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza is caused by one or more influenza viruses selected from influenza A virus, influenza B virus, and influenza C virus; preferably, the influenza A virus is an influenza A virus of H1N1 subtype, H2N2 subtype, H3N2 subtype, H5NI subtype, H7N9 subtype or H9N2 subtype.

In one embodiment of the present invention, the subject is a mammal (e.g., a human, a simian, a monkey, a pig, a cow or a sheep) or a bird (e.g., a domestic bird such as a chicken, a duck or a goose, or e.g, a wild bird).

In one embodiment of the present invention, the influenza symptom is at least one selected from the following symptoms caused by influenza:

fever, cough, headache, muscle pains, and diarrhea.

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

The present invention further relates to a method of protecting against an influenza virus (e.g., inhibiting replication of an influenza virus in a host cell), including a step of administering an effective amount of a product selected from any one of (1) to (3) to a subject in need:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza virus is selected from one or more of influenza A virus, influenza B virus, and influenza C virus; preferably, the influenza A virus is an influenza A virus of H1N1 subtype, H2N2 subtype, H3N2 subtype, H5NI subtype, H7N9 subtype or H9N2 subtype.

In one embodiment of the present invention, the subject is a mammal (e.g., a human, a simian, a monkey, a pig, a cow or a sheep) or a bird (e.g., a domestic bird such as a chicken, a duck or a goose, or e.g, a wild bird).

In one embodiment of the present invention, the host cell is a cell of a mammal (e.g., a human, a simian, a monkey, a pig, a cow or a sheep) or a bird (e.g., a domestic bird such as a chicken, a duck or a goose, or e.g, a wild bird).

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

The present invention further relates to a method of inhibiting replication of an influenza virus RNA polymerase, inhibiting the expression level of an influenza virus RNA polymerase or inhibiting the activity of an influenza virus RNA polymerase, including a step of administering an effective amount of a product selected from any one of (1) to (3) to a subject in need:

(1) cannabidiol or a pharmaceutically acceptable salt or ester thereof;

(2) a plant extract containing cannabidiol; preferably, a cannabis extract containing cannabidiol; preferably, an industrial cannabis extract containing cannabidiol; and (3) a pharmaceutical composition, containing an effective amount of cannabidiol or a pharmaceutically acceptable salt or ester thereof, and one or more pharmaceutically acceptable auxiliary materials.

In one embodiment of the present invention, the influenza virus RNA polymerase is selected from one or more of an influenza A virus RNA polymerase, an influenza B virus RNA polymerase, and an influenza C virus RNA polymerase; preferably, the influenza A virus RNA polymerase is an RNA polymerase of an influenza A virus of H1N1 subtype, H2N2 subtype, H3N2 subtype, H5NI subtype, H7N9 subtype or H9N2 subtype.

In one embodiment of the present invention, the subject is a mammal (e.g., a human, a simian, a monkey, a pig, a cow or a sheep) or a bird (e.g., a domestic bird such as a chicken, a duck or a goose, or e.g, a wild bird).

In one embodiment of the present invention, the pharmaceutical composition further includes an effective amount of one or more ingredients selected from:

an inosine monophosphate dehydrogenase inhibitor, an interferon inducer, an M2 ion channel protein inhibitor and a neuraminidase inhibitor;

preferably, the inosine monophosphate dehydrogenase inhibitor is ribavirin;

preferably, the interferon inducer is arbidol hydrochloride;

preferably, the M2 ion channel protein inhibitor is amantadine hydrochloride or rimantadine hydrochloride; and preferably, the neuraminidase inhibitor is oseltamivir phosphate, oseltamivir, zanamivir or peramivir.

It should be noted that the dosage and methods of use of the active ingredient cannabidiol depends on a number of factors, including the patient's age, body weight, sex, natural health status and nutritional status, the activity intensity, time of administration and rate of metabolism of the compound, severity of the condition, and subjective judgment of the doctor. According to any one of the methods in the present invention, the dosage of cannabidiol is 0.1-50 mg/kg body weight/day, more preferably 0.5 mg/kg-30 mg/kg body weight/day, 0.5 mg/kg-20 mg/kg body weight/day, 5 mg/kg-30 mg/kg body weight/day or 5 mg/kg-20 mg/kg body weight/day, further preferably 0.5 mg/kg-10 mg/kg body weight/day, particularly preferably 0.5 mg/kg-5 mg/kg body weight/day.

According to any one of the methods in the present invention, the administration is oral administration.

In the present invention, the cannabidiol, that is, a compound of the formula I, can be purchased commercially (e.g., purchased from Sigma, etc.) or synthesized by using commercially available materials by the prior art. After the synthesis, the synthesized cannabidiol can be further purified by column chromatography, liquid-liquid extraction, molecular distillation or crystallization, and the like. In addition, the cannabidiol can also be extracted from cannabis, especially industrial cannabis.

The pharmaceutically acceptable salt of cannabidiol includes, but is not limited to, an organic ammonium salt, an alkali metal salt (a sodium salt, a potassium salt), an alkaline earth metal salt (a magnesium salt, a strontium salt, a calcium salt), and the like.

In some embodiments of the present invention, the pharmaceutically acceptable salt of cannabidiol may be a salt formed from cannabidiol (CBD) and sodium hydroxide, potassium hydroxide, calcium hydroxide, magnesium hydroxide, aluminum hydroxide, lithium hydroxide, zinc hydroxide, barium hydroxide, ammonia, methylamine, dimethylamine, diethylamine, picoline, ethanolamine, diethanolamine, triethanolamine, ethylenediamine, lysine, arginine, ornithine, choline, N,N'-diphenylmethylethylenediamine, chloroprocaine, diethanolamine, procaine, N-benzylphenethylamine, N-methylglucamine, piperazine, tris(hydroxymethyl)-aminomethane or the like.

In some embodiments of the present invention, the pharmaceutically acceptable ester of cannabidiol may be a monoester formed from cannabidiol and a $C_0$-$C_6$ alkyl carboxylic acid, or may be a diester formed from cannabidiol and two identical or different $C_0$-$C_6$ alkyl carboxylic acids, and the $C_0$-$C_6$ alkyl carboxylic acid may be a linear alkyl carboxylic acid, a branched alkyl carboxylic acid or a cycloalkyl carboxylic acid, for example, HCOOH, $CH_3COOH$, $CH_3CH_2COOH$, $CH_3(CH_2)_2COOH$, $CH_3(CH_2)_3COOH$, $CH_3(CH_2)_4COOH$, $(CH_3)_2CHCOOH$, $(CH_3)_3CCOOH$, $(CH_3)_2CHCH_2COOH$, $(CH_3)_2CH(CH_2)_2COOH$, $(CH_3)_2CH(CH_3)CHCOOH$, $(CH_3)_3CCH_2COOH$, $CH_3CH_2(CH_3)_2CCOOH$, cyclopropanecarboxylic acid, cyclobutanecarboxylic acid or cyclopentanecarboxylic acid.

The cannabis extract may be an extract of cannabidiol-containing cannabis, especially industrial cannabis, for example, an ethanol extract, an extractum, or the like. The content of cannabidiol is not particularly limited, and the content of cannabidiol in the cannabis extract can be further increased by means known to those skilled in the art such as concentration. In one embodiment of the present invention, the cannabis extract is an extractum, preferably wherein the content of cannabidiol is 18%-25%.

In some embodiments of the present invention, the cannabis extract is an extract obtained by using any one or more selected from stems, leaves, fruits, husks, roots, and flowers of cannabis as a raw material. Preferably, the cannabis extract is a cannabis leaf extract.

In the present invention, the term "effective amount" refers to a dosage that can achieve treatment, prevention, alleviation and/or relief of the disease or condition of the present invention in a subject.

The term "subject" can refer to a patient or other animals that receive the composition of the present invention to treat, prevent, alleviate and/or relieve the disease or condition of the present invention, particularly a mammal, such as a human, a dog, a monkey, a cow, a horse or the like.

The term "disease and/or condition" refers to a physical state of the subject that is associated with the disease and/or condition of the present invention.

In the present invention, unless otherwise specified, the product 1 and the product 2 are merely for the sake of clarity and do not have the meaning of order.

In the present invention, unless otherwise specified, the cannabis is preferably industrial cannabis; and the cannabis extract is preferably an industrial cannabis extract.

BENEFICIAL EFFECTS OF THE INVENTION

The cannabidiol can effectively inhibit influenza viruses, and has the potential to prepare or be used as a drug for treating or preventing influenza.

BRIEF DESCRIPTION OF THE DRAWINGS

FIG. 3: Changes in behavior of WSN-infected mice. After the mice were infected with WSN, the behavior was continuously monitored for 10 days. Data are expressed as mean±standard error (n=5/group). Significance analysis was performed on differences by using a post hoc method, with significant differences expressed as *, $p<0.01$, $*p<0.001$. FIG. 3A, Day 6 after H1N1 infection. FIG. 3B, Day 8 after H1N1 infection.

FIG. 4: Changes in mortality of WSN-infected mice. After the mice were infected with WSN, the number of surviving mice was continuously monitored for 12 days. Data are expressed as mean±standard error. Each point represents the number of surviving mice, (n=20/group). Significance analysis was performed on differences by using a post hoc method.

FIG. 6: Changes in lung pathology of WSN-infected mice. The mice on Day 8 after infection were taken and the pathological analysis of the lungs was detected.

DETAILED DESCRIPTION OF THE EMBODIMENTS

Figure 1:
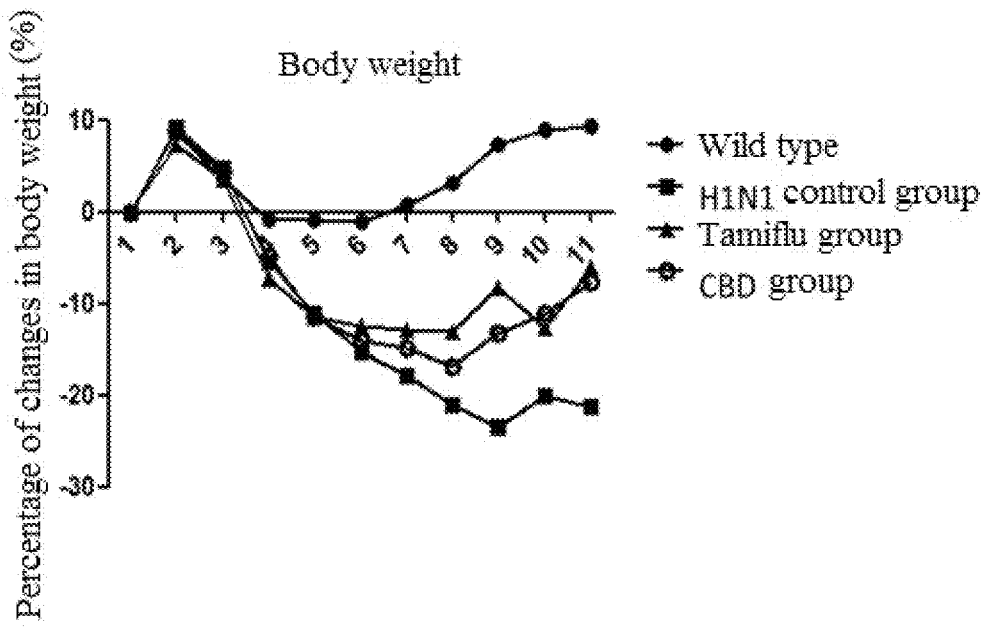
FIG. 1: Changes in body weight of WSN-infected mice. After the mice were infected with WSN, the body weight was continuously monitored for 11 days. Data are expressed as mean±standard error. Each point represents the mean daily change in body weight of the mice, (n=20/group). Significance analysis was performed on differences by using a post hoc method, with significant differences expressed as *, **, $p<0.01$.

Embodiments of the present invention will be described in detail below with reference to the examples. However, those skilled in the art will understand that the following examples are merely illustrative of the present invention and should not be construed as limiting the scope of the present invention. The examples in which specific conditions are not specified are carried out according to conventional conditions or conditions recommended by the manufacturer. Those reagents or instruments of which manufacturers are not given are conventional products that are commercially available.

In the following examples, unless otherwise specified:

The H1N1 WSN (A/WSN/33) strain and the H5N1 A/great black-headed gull/Qinghai/2009 (H5N1) strain of IAV were provided by the Institute of Microbiology, Chinese Academy of Sciences.

Experiments involving H1N1 were performed in biosafety level 2 laboratories, and experiments involving H5N1 were performed in biosafety level 3 laboratories.

EXAMPLE 1: ANIMAL EXPERIMENT OF CANNABIDIOL AGAINST INFLUENZA A VIRUS H1N1

1. Experimental Animals and Preliminary Preparation 6-week-old Kunming white male mice, purchased from Beijing Vital River Laboratory Animal Technology Co., Ltd.

The animals were routinely raised at the P2 and P3 animal centers (Biosafety levels 2 and 3, P2/P3) of the Institute of Microbiology, Chinese Academy of Sciences. The light cycle was 12 h light/12 h dark, and the animals had free access to food and water. Related experiments were performed after the animals were acclimated to the new environment for 1 day. The China Agricultural University and the Animal Ethics Committee of the State Key Laboratory of Agrobiotechnology (SKLAB-2017-3-002) approved the animal experiments.

9 to 11-day-old SPF embryonated chicken eggs purchased from Beijing Merial Vital Laboratory Animal Technology Co., Ltd.

2. Experimental Methods (1) H1N1 Influenza Virus Amplification in Embryonated Chicken Eggs The 9 to 11-day-old SPF embryonated chicken eggs were candled, the position of the air cell of each egg was marked, and the position where there were fewer blood vessels was marked.

The egg shell was disinfected with iodophor and 70% ethanol; a hole was punched 2-3 mm above the mark, and 200 μl of influenza virus diluted moderately with PBS was injected into the allantoic cavities of the embryonated chicken eggs; the hole was sealed with wax.

The eggs were inoculated at 37° C. for 48 h-72 h, the survival of the embryonated chicken eggs was observed once every 24 h, if the embryonated chicken eggs were observed to die, the embryonated chicken eggs were placed at 4° C. overnight and the allantoic fluid was collected, and by 72 h, the remaining embryonated chicken eggs were placed at 4° C. overnight and the allantoic fluid was collected.

Method of collecting allantoic fluid: Sterile tweezers were used to break the shell above the air cell of the egg, the chorioallantoic membrane above the air cell was torn open, and the allantoic fluid was slowly sucked with a 1 ml pipette.

The harvested allantoic fluid was centrifuged at 2000-3000 rpm for 10 min, and the supernatant was sucked to obtain the virus. The virus was stored at −80° C. for later use.

(2) Titer Testing of H1N1 Influenza Virus on MDCK Cell Line

MDCK cells (Madin-Daby canine kidney cells, purchased from ATCC, USA) were cultured. When the confluence reached 95%, the MDCK cells were infected with the H1N1 strain of the virus amplified in the embryonated chicken eggs above and proliferated, and then were centrifuged, the supernatant was collected to obtain a virus stock solution, and virus titer measurement was performed.

(3) Animal Grouping

The results of the preliminary 6 pre-tests of the inventors showed that in the Tamiflu group (20 mg/kg/d) and the two CBD injection groups (20 mg/kg/d and 60 mg/kg/d), the mortality of mice caused by IAV infection could be significantly inhibited. Nasal inhalation of H1N1 (12000 pfu) could cause 95% of mice to die, and the two CBD injection groups (20 mg/kg/d and 60 mg/kg/d) inhibited the same mortality in mice caused by IAV infection. Nasal inhalation of H5N1 (1000 pfu) could cause 95% of mice to die, and the two CBD injection groups (20 mg/kg/d and 60 mg/kg/d) inhibited the same mortality in mice caused by IAV infection.

Therefore, for safety reasons, the grouping and administration and model preparation of formal experiments were carried out with H1N1 WSN virus as the infection strain. The Kunming white male mice were randomly divided into 4 groups, 20 mice in each group. From Day 4 after infection, the drug was administered once a day by intraperitoneal injection for 5 consecutive days. The blank group and the 12000 pfu influenza group were injected with the same amount of normal saline. The specific grouping is as follows:

Blank group (wild type): not infected, and injected with the same amount of normal saline from Day 4.

12000 pfu influenza group (high toxicity group): injected with the same amount of normal saline from Day 4 after infection.

Tamiflu group: administered from Day 4 after infection (Tamiflu, 20 mg/kg/d).

CBD group: administered from Day 4 after infection (cannabidiol, 20 mg/kg/d).

Infection operation procedure: after mildly anesthetizing the mice with diethyl ether, the mice were intranasally administrated with an H1N1 influenza virus solution (the virus stock solution previously stored at −80° C. diluted in PBS at 1:120), 0.05 ml per mouse, and the blank group was intranasally administered with the same amount of normal saline.

(4) Observation and Recording of Physiological Characteristics and Onset Symptoms of Mice The body weight and temperature of the mice at different times were recorded, the onset symptoms of the mice were observed, and the time of death and the number of deaths of the mice were recorded. Observation was performed until 14 days after infection.

1) Measurement of body weight: a suitable beaker was placed on an electronic scale, the reading was zeroed, the mouse was placed into the beaker, and the reading was recorded when it was stable. The mice were weighed once every 24 hours.

From 0 day of post infection (DPI 0) of H1N1 (WSN) to 10 days of post infection (DPI 10), the mice were weighed daily, and the body weight change percentage was calculated by subtracting the body weight on DPI 0 from the body weight of the day and dividing the difference by the body weight on DPI 0.

2) Measurement of body temperature: body temperature drop caused by H1N1

At the same time, an 8000 pfu influenza group was additionally set for measurement of body temperature only.

The mice were infected with WSN at a dose of 8000 pfu, and the changes in body temperature were monitored. The infected mice, 5 in each group, were subjected to rectal temperature measurement daily on DPI 0 to DPI 12, and the percentage of changes in body temperature was calculated by subtracting the rectal temperature on DPI 0 from the rectal temperature of the day and dividing the difference by the rectal temperature on DPI 0.

The mice were caught by a correct operation method. That is, the abdomen was faced to the operator, an electronic thermometer sensor was dipped in vegetable oil and inserted straight into the anus of the mouse, and the body temperature was measured when the probe just entered the anus completely. The body temperature of the mice was measured once every other 24 hours.

3) A video of each group was recorded regularly (2 minutes for each group, n=6). The quantification of mouse activity status is given in Table 1 below.

TABLE 1

Operation instructions on behavioral actions in RAPID behavioral action classification method

| | Description |
|---|---|
| Main body posture | |
| Standing | The rat stands on four limbs, and the body does not move |
| Sitting | The front half of the body is raised, the front and rear of the body are almost at a right angle, and the rear of the body is on the ground |
| Standing up | The rat stands up with hind legs, the body tends to be vertical, and the front is raised |
| Walking | The rat walks on four limbs |
| Lying down | The abdomen of the body is on the ground, and the body does not move (at least 5 pictures are required) |
| Grooming actions | |
| Blank Grooming | Grooming is not recognizable |
| Grooming | The mouth and the soles touch the body |
| Head turning | The head moves horizontally by more than 15° |
| Watching | The head is upward without facing a target, and the body does not move |
| Smelling | The nose observes a hole in the cage wall |
| Sniffing | The nose faces a target: the ground or the wall, and the body does not move |
| Rotating | The head and the body move horizontally by more than 20° |
| Face washing | The forepaw moves on the head |

On DPI 6 and DPI 8 of the challenge, the activity status of the mice was respectively recorded in a video, detected and quantified. Changes in mouse behavior are divided into main actions and grooming actions (standing, sitting, standing up, walking, lying down, head turning, watching, smelling, face washing, etc.). For details, references are made to sections of the experimental materials and methods. Representative behavioral actions within 2 minutes were taken.

4) Calculation of survival rate

The number of surviving mice in each group was observed and recorded every day.

Survival rate of each group=number of surviving individuals in each group/total number of individuals in each group×100%.

The daily survival rate of each group of mice was calculated and summarized, and a chart was drawn for analysis of their trend of death.

(5) Mouse Lung Index and Spleen Index

On DPI 8, 5 mice in each group were tested for the lung index and spleen index. On Day 8 of IAV infection, the mice were anesthetized with 150-200 μl of pentobarbital, the body weight of the mice was measured, blood was taken from the eyeballs, and then the mice were fixed on a dissecting plate, The mice were dissected along the midline of the abdomen, and the heart, lung, liver, spleens and lymph node were taken down in turn. Half of the lung was taken for measurement of lung weight, and the total weight of the spleens was measured (water on the surfaces of the lung and spleens was removed as much as possible by using absorbent paper). Then, the lung and the spleen were fixed in polyformaldehyde for sectioning.

The lung index and inhibition rate were calculated according to the following formulae:

$$\text{Lung index} = \frac{\text{Mouse lung weight (g)}}{\text{Mouse body weight (g)}} \times 100\%$$

Lung index inhibition rate =

$$\frac{\text{Model group lung index} - \text{Experimental group lung index}}{\text{Model group lung index}} \times 100\%$$

(6) Observation of Pathological Section of Lung Tissue

After the lung weight was measured, the lung tissue was immersed in 10% formaldehyde for fixation and then immersed in alcohol of a concentration gradient for 2-4 h to remove the water in the tissue block, and placed in a clearing agent xylene for 0.5-2 h. The cleared tissue block was embedded in paraffin and fixed on a microtome, and cut into thin slices (about 4-5 μm in thickness). The paraffin in the section was removed with xylene, the section was stained with hematoxylin and eosin (HE), and the pathomorphological changes of the lung tissue were observed under an optical microscope Olympus CX 41 (Olympus, Japan).

(7) Vascular Permeability Test

On DPI 8, 5 mice in each group were tested for pulmonary vascular permeability. The mice were anesthetized, and an Evans Blue solution was injected through the tail vein. After 5 min, the alveolar lavage fluid was taken and centrifuged at 1500 rpm for 5 min. The supernatant was taken, and the absorbance OD at 590 nm was measured by a spectrophotometer.

(8) Acquisition of Mouse Alveolar Lavage Fluid and Diff-Quick Staining

On DPI 8, 5 mice in each group were tested for the number of inflammatory cells in the alveolar lavage fluid. Compared with the high toxicity treatment group, in the CBD group (20 mg/kg/d), the number of neutrophils in the alveolar lavage fluid of mice caused by H1N1 WSN infection could be significantly reduced.

The mice were anesthetized, the eyeballs were bled or blood was taken from the heart.

The skin of the mouse neck was cut open to expose the trachea.

A small opening was cut in the trachea, and 1 mL of PBS containing 0.1 mM EDTA was injected, sucked back and collected in a 10 mL centrifuge tube. The operations were repeated for three times to obtain about 3 mL of lavage fluid.

The lavage fluid was centrifuged at 1500 rpm for 5 min. The supernatant was transferred to a new 10 mL centrifuge tube and cryopreserved at −80° C. The cell pellet was resuspended in 450 μl of ddH$_2$O and gently shaken for no more than 1 min. The red blood cells were rapidly lysed and 50 μL of 10×PBS was immediately added.

Centrifugation was performed at 1500 rpm for 5 min, the supernatant was removed, and PBS was added for resuspension.

Counting was performed with a hemocytometer.

After the counting was completed, centrifugation was performed, the supernatant was removed, and the cells were resuspended in serum, and smeared.

Diff-Quick staining: The wet (i.e., not dried) smear is immersed in an ethanol-diethyl ether solution for fixation for 15 seconds. The fixing solution at the edge was slightly removed, the smear was dipped in Diff-Quick I and Diff-Quick II solutions respectively for 15 seconds, and the excess dye was washed away with running water.

The wet smear (i.e., not dried) was detected under a microscope and the counting was performed, and the ratio of various cells was calculated.

(9) Statistical Analysis on Data of Experimental Results Above

One-way ANOVA was performed by using SPSS 12.0.1 data processing software (SPSS Inc., Chicago, Ill.), the data was in accordance with the normal distribution, and the significance test was performed by using a t test. Data were expressed as mean±standard error, $p<0.05$ for significant difference; $p<0.01$ for extremely significant difference.

3. Experimental Results

(1) In the CBD Injection Group, the Body Weight Drop Caused by H1N1 Could be Significantly Inhibited As shown in FIG. 1.

As can be seen from the figure, the initial fluctuation of body temperature in mice was due to the stress response that occurred when the mice were purchased for experimentation and acclimated to the new environment. However, since the initial body weight percentage curves of of mice in the groups are roughly equivalent, the change caused by the stress response can be ignored. The body weight of the mice began to drop significantly on Day 3 after the infection with influenza virus, reached the lowest point on about Day 7 to Day 8, and then began to rise. The body weight of the individual that did not die in 7 days began to rise significantly. Compared with the high toxicity group, in the Tamiflu group (20 mg/kg/d) and the CBD group (20 mg/kg/d), the body weight drop could be significantly inhibited ($p<0.01$).

Figure 2:
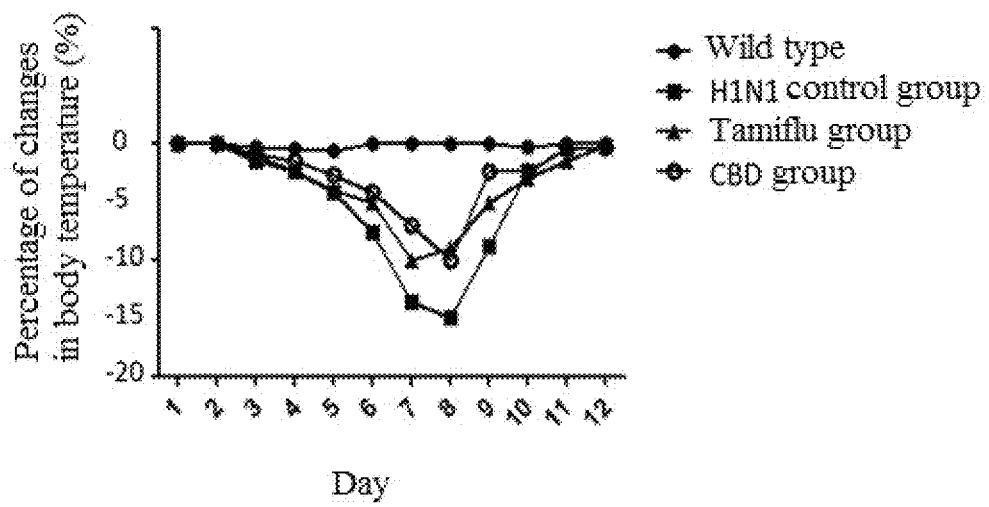
FIG. 2: Changes in body temperature of WSN-infected mice. After the mice were infected with WSN, the body temperature was continuously monitored for 12 days. Data are expressed as mean±standard error. Each point represents the mean daily change in body temperature of the mice (n=15-20/group). Significance analysis was performed on differences by using a post hoc method, with significant differences expressed as *, $*p<0.05$.
Figure 5:
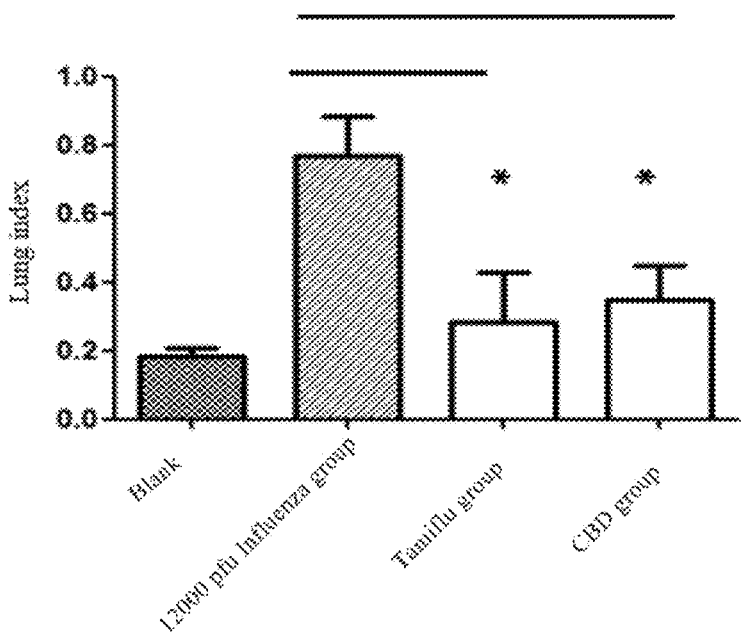
FIG. 5: Changes in lung index of WSN-infected mice. The mice on Day 8 after infection were taken and the lung infection was detected. Data are expressed as mean±standard error, $*p<0.05$.
Figures 6A, 6B, 6C, 6D:
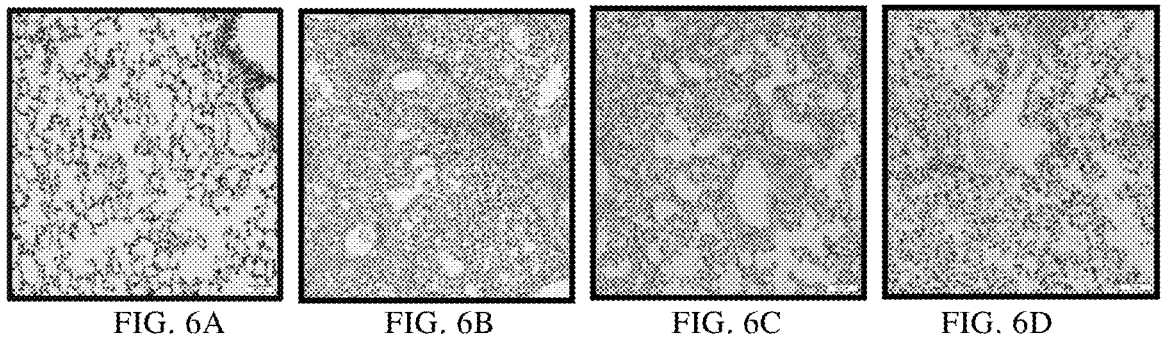
FIG. 6A, wild control.
FIG. 6B, influenza infected lung control.
FIG. 6C, Tamiflu treatment group.
FIG. 6D, CBD treatment group.

(2) In the CBD Injection Group, the Body Temperature Drop Caused by H1N1 Could be Significantly Inhibited As shown in FIG. 2.

There was a significant difference in changes in body temperature of mice on DPI 7 to DPI 9, with the greatest change on DPI 7 to DPI 8. As can be seen from the figure, the body temperature of the mice on Day 4 after the infection with IAV began to drop significantly, reached the lowest point on about Day 7 to Day 8, and then began to rise. The body temperature of the individual that did not die in 7 days began to rise significantly. Compared with the high toxicity group, in the Tamiflu group (20 mg/kg/d) and the CBD group (20 mg/kg/d), the body temperature drop could be significantly inhibited.

(3) In the CBD Group, the Influenza Symptoms and Behavioral Discomfort in the H1N1 Infected Group Could be Significantly Reduced As shown in FIG. 3A and FIG. 3B.

On DPI 6 to DPI 9, there was a significant difference in the changes in behavior of mice, with the greatest change on DPI 8. Compared with the high toxicity treatment group, in the Tamiflu group (20 mg/kg/d) and the CBD injection group (20 mg/kg/d), the activities of the infected mice could be significantly increased, and the discomfort caused by influenza could be significantly alleviated.

(4) In the CBD Injection Group, the Mortality of the H1N1 Infected Group Could be Significantly Reduced As shown in FIG. 4.

Compared with the high toxicity treatment group, in the Tamiflu group (20 mg/kg/d) and the CBD group (20 mg/kg/d), the mortality of mice caused by H1N1 WSN infection could be significantly reduced (Tamiflu group, $P<0.001$; CBD group, $P<0.001$). 9 mice died in the Tamiflu treatment group (9/20), and 10 mice died in the CBD group (10/20). The CBD group showed very significant therapeutic effects. There was no significant difference in mortality in the Tamiflu group (9/20) and the CBD group (10/20).

(5) In the CBD Group, the Lung Injury in the H1N1 Infected Group Could be Significantly Reduced As shown in FIG. 5 and FIGS. 6A to 6D.

Compared with the high toxicity group, in the Tamiflu group (20 mg/kg/d) and the CBD group (20 mg/kg/d), the lung injury index of mice caused by H1N1 WSN infection could be significantly reduced (Tamiflu group, $P<0.05$; CBD group, $P<0.05$). The CBD group showed very significant therapeutic effects. There was no significant difference in lung index in the Tamiflu group (9/20) and the CBD group (10/20). In the Tamiflu and CBD treatment groups, the inflammatory cell infiltration could be significantly reduced.

Figure 7:
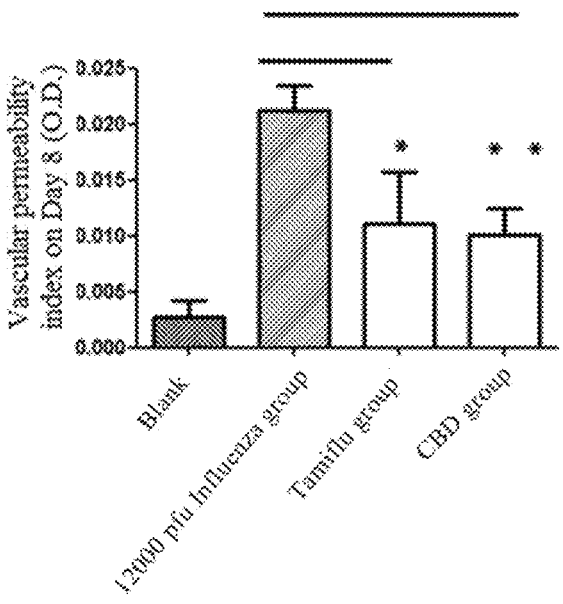
FIG. 7: Changes in lung index of WSN-infected mice. The mice on Day 8 after infection were taken and the pulmonary vascular permeability was detected. Data are expressed as mean±standard error, $*p<0.05$; $**p<0.01$.

(6) In the CBD group, the pulmonary vascular permeability of the H1N1 infected group could be significantly reduced As shown in FIG. 7.

Compared with the high toxicity group, in the Tamiflu group (20 mg/kg/d) and the CBD injection group (20 mg/kg/d), the mouse pulmonary capillary permeability caused by H1N1 WSN infection could be significantly reduced, and the lung injury could be significantly reduced. Tamiflu group, *$P<0.05$; CBD group, **$P<0.01$.

Figure 8:
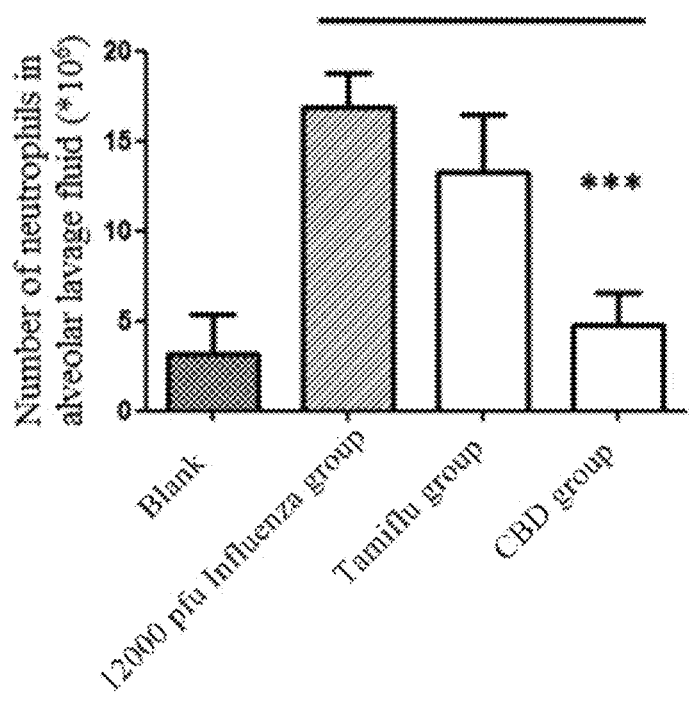
FIG. 8: Changes in neutrophils in alveolar lavage fluid of WSN-infected mice. The mice on DPI 8 were taken and the number of neutrophils in the alveolar lavage fluid was measured. Data are expressed as mean±standard error, $***p<0.001$.

(7) In the CBD Group, the Number of Inflammatory Cells in the Alveolar Lavage Fluid of the H1N1 Infected Group Could be Significantly Reduced As shown in FIG. 8. In the CBD group, $P<0.001$. Compared with the Tamiflu group, the CBD group showed a very significant reduction in the number of neutrophils in the alveolar lavage fluid.

Figure 9:
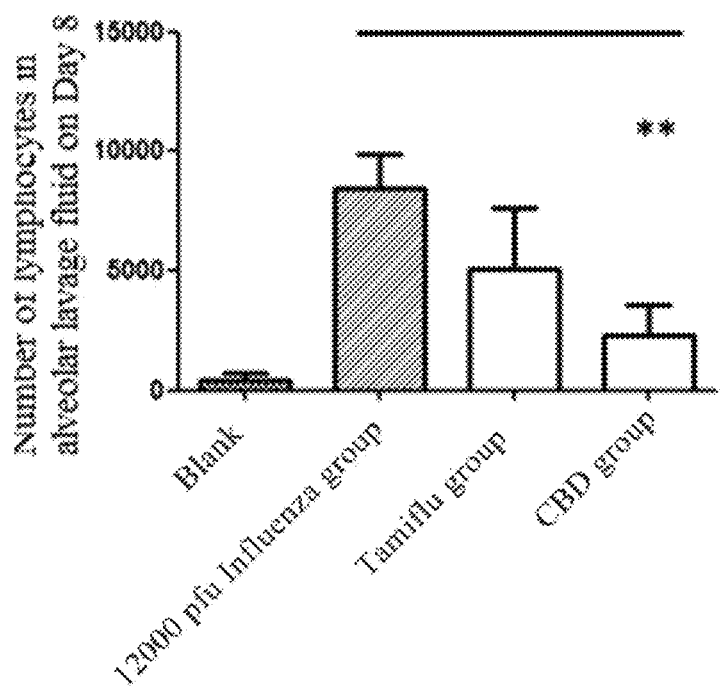
FIG. 9: Changes in lymphocytes in alveolar lavage fluid of WSN-infected mice. The mice on DPI 8 were taken and the number of lymphocytes in the alveolar lavage fluid was measured. Data are expressed as mean±standard error, $**p<0.01$.

As shown in FIG. 9. Compared with the IAV treatment group, in the CBD group, $P<0.01$. The number of lymphocytes in the alveolar lavage fluid was significantly reduced.

Figure 10:
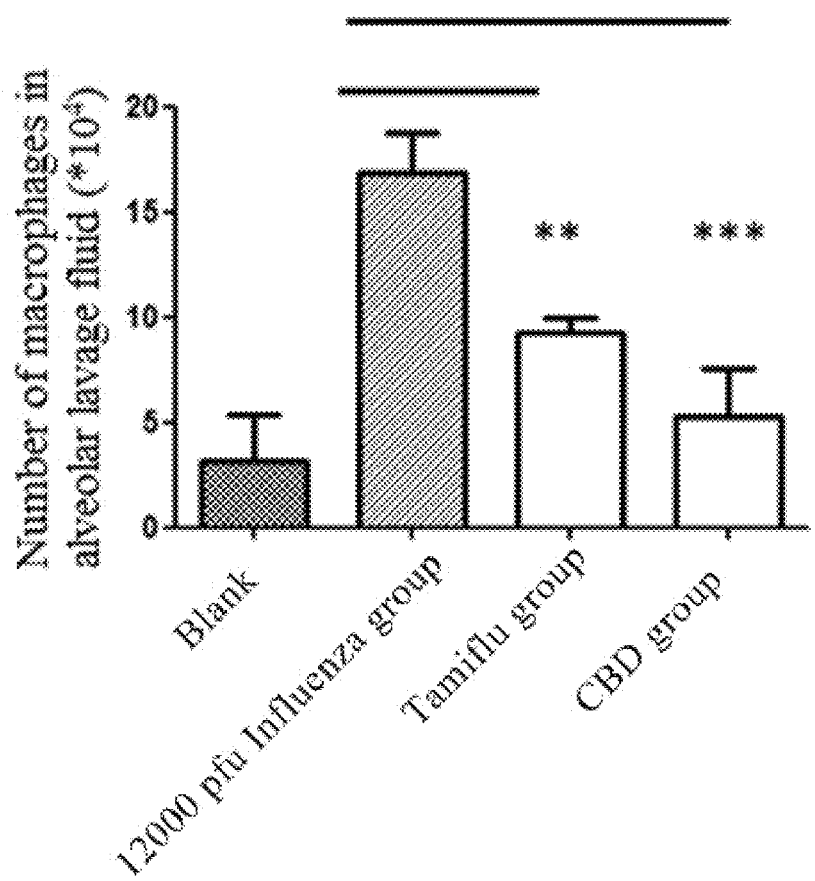
FIG. 10: Changes in macrophages in alveolar lavage fluid of WSN-infected mice. The mice on DPI 8 were taken and the number of macrophages in the alveolar lavage fluid was measured. Data are expressed as mean±standard error, $p<0.01$, $*p<0.001$.

As shown in FIG. 10. In the Tamiflu group, $P<0.01$; in the CBD group, $P<0.001$. The number of macrophages in the alveolar lavage fluid was significantly reduced. Compared with the Tamiflu group, the CBD group also showed a significant reduction in the number of macrophages in the alveolar lavage fluid, $P<0.05$.

The above experimental results show that:

CBD can significantly reduce the influenza symptoms and discomfort of mice caused by H1N1 WSN infection, can significantly inhibit the drop in body weight and body temperature of mice, and reduces the mortality of mice caused by influenza. CBD also reduces the pulmonary vascular permeability, reduces the infiltration of inflammatory cells (neutrophils, lymphocytes, macrophages) in the lung tissue of influenza-infected mice, and reduces the acute lung injury (ALI).

EXAMPLE 2: IN VITRO EXPERIMENT OF CANNABIDIOL INHIBITING RNA POLYMERASE OF INFLUENZA A VIRUS H1N1

6-well plates were inoculated with subcultured mouse bone marrow-derived macrophages (BMDM) and a human non-small cell lung cancer cell line A549 (ATCC® CCL-185™), which was divided into the following 4 groups:

control group (high glucose medium DMEM, of which the manufacturer is Sigma and the product code is D5648-1L, diluted to 1 liter with purified water before the experiment), H1N1 infected control group, CBD group (5 µM) and Tamiflu group (10 µM).

The above four groups were cultured overnight at 37° C., and when the cell confluence reached 100% after 18-24 h and there was no gap between cells, the cells were infected with H1N1 WSN. At an MOI of 0.01, the cells were infected for 1 h.

The supernatant was sucked and discarded, and the same volume of serum-free medium containing PBS, Tamiflu and CBD was correspondingly added to each group, wherein each serum-free medium contained the same concentration of PBS, Tamiflu and CBD. Incubation was performed in a $CO_2$ incubator at 37° C. for 24 h.

RNA was extracted, and reversely transcribed, and qRT-PCR was used to detect the expression of virus mRNA. RT-PCR primers for detecting expression of NP, PA, PB1 and PB2 genes in H1N1 are as follows:

```
NP-F1:
                                    (SEQ ID NO: 1)
CGGGGAGTCTTCGAGCTCTC

NP-R1:
                                    (SEQ ID NO: 2)
TTGTCTCCGAAGAAATAAGA

PA-F1:
                                    (SEQ ID NO: 3)
ATGGAAGATTTTGTGCGACA

PA-R1:
                                    (SEQ ID NO: 4)
TGACTCGCCTTGCTCATCGA
```

-continued

PB1-F1:
TACCGGTGCCATAGAGGTGA (SEQ ID NO: 5)

PB1-R1:
CGCCCTGGTAATCCTCATC (SEQ ID NO: 6)

PB2-F1:
GCGATTGAATCCCATGCACC (SEQ ID NO: 7)

PB2-R1:
TCCGCGCTGGAATACTCATC (SEQ ID NO: 8)

Figure 11A:
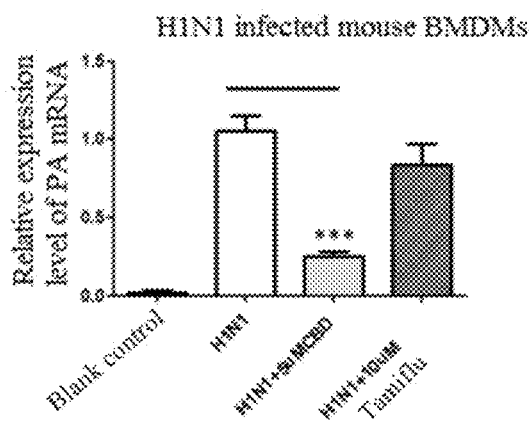
FIG. 11A: Changes in expression of PA gene in CBD-treated WSN-infected mouse BMDMs. Changes in expression of PB1 gene in CBD-treated H1N1-infected mouse BMDMs after 24 h. Data are expressed as mean±standard error, $*p<0.05$.
Figure 11B:
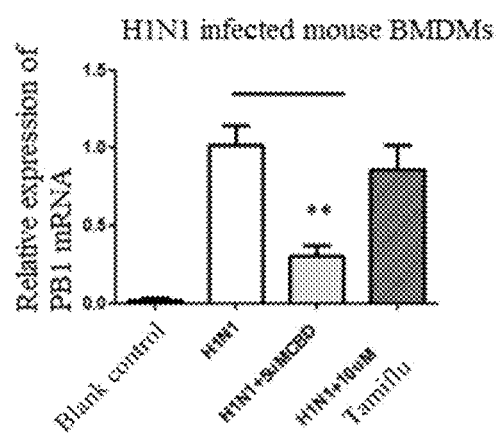
FIG. 11B: Changes in expression of PB1 gene in CBD-treated WSN-infected mouse BMDMs. Changes in expression of PB1 gene in CBD-treated H1N1-infected mouse BMDMs after 24 h. Data are expressed as mean±standard error, $*p<0.05$.
Figure 12A:
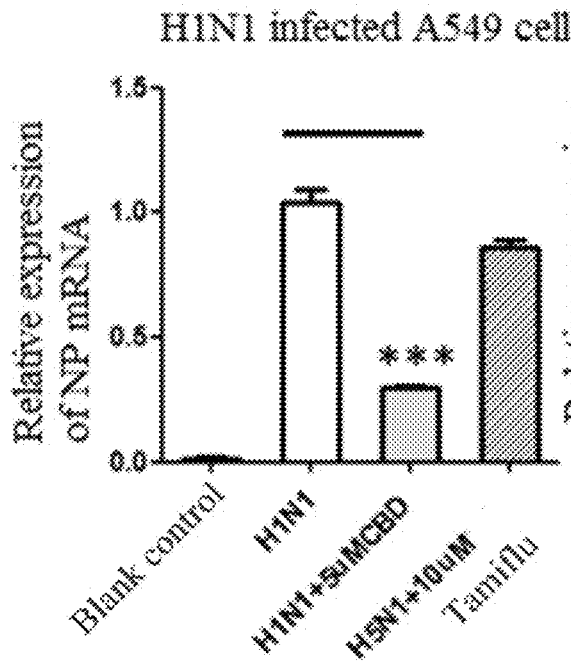
FIG. 12A: Changes in expression of NP gene in a CBD-treated H1N1-infected human lung epithelial cell line A 549. Changes in expression of NP gene in a CBD-treated H1N1-infected human lung epithelial cell line A 549 after 24 h. Data are expressed as mean±standard error, $***p<0.001$.
Figure 12B:
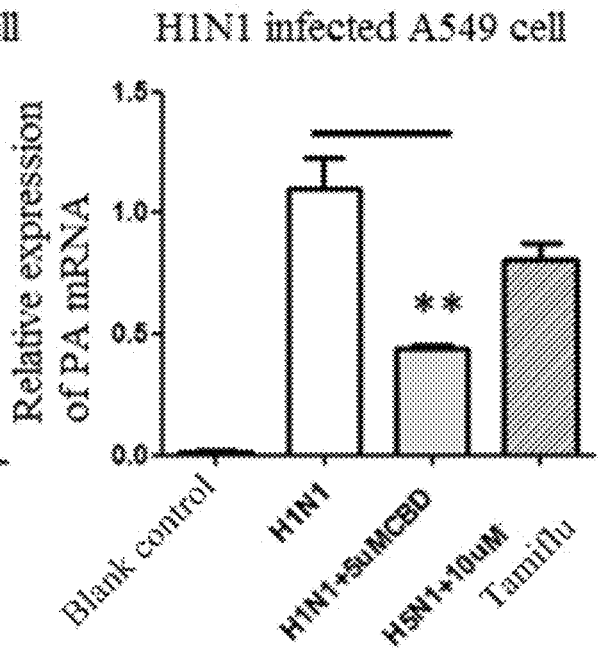
FIG. 12B: Changes in expression of PA gene in a CBD-treated H1N1-infected human lung epithelial cell line A 549. Changes in expression of PA gene in a CBD-treated H1N1-infected human lung epithelial cell line A 549 after 24 h. Data are expressed as mean±standard error, $**p<0.01$.
Figure 12C:
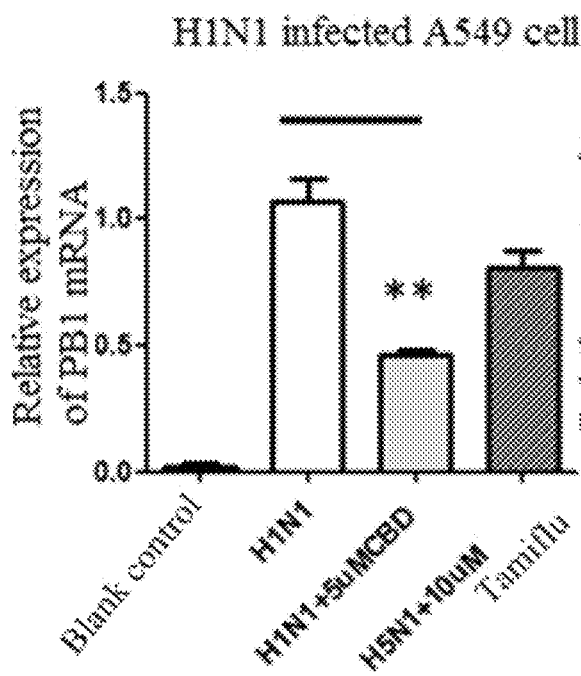
FIG. 12C: Changes in expression of PB1 gene in a CBD-treated H1N1-infected human lung epithelial cell line A 549. Changes in expression of PB1 gene in a CBD-treated H1N1-infected human lung epithelial cell line A 549 after 24 h. Data are expressed as mean±standard error, **$p<0.01$.
Figure 12D:
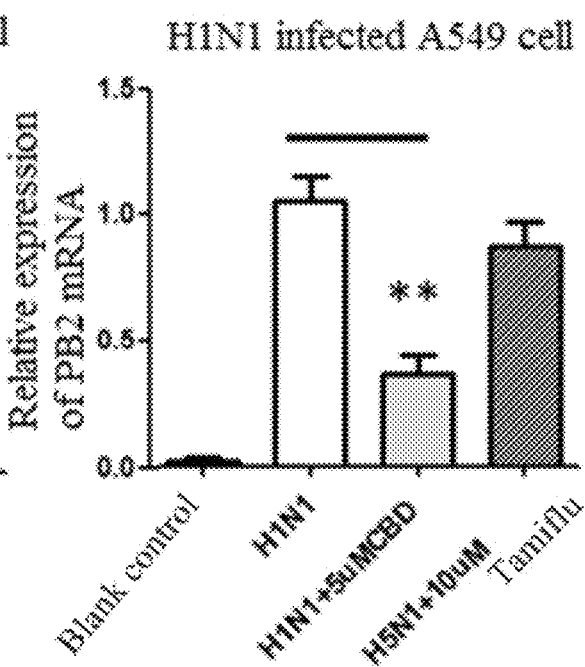
FIG. 12D: Changes in expression of PB2 gene in a CBD-treated H1N1-infected human lung epithelial cell line A 549. Changes in expression of PB2 gene in a CBD-treated H1N1-infected human lung epithelial cell line A 549 after 24 h. Data are expressed as mean±standard error, **$p<0.01$.

The experimental results are shown in FIG. 11A and FIG. 11B (BMDMs of mice) and FIG. 12A to FIG. 12D (human lung epithelial cell line A 549) respectively.

The results showed that in the Tamiflu group (10 μM), there was no significant inhibitory effect on the expression of NP, PA, PB1 and PB2 genes in H1N1 WSN. Surprisingly, in the CBD group (5 μM), the expression of NP, PA, PB1 and PB2 genes in H1N1 WSN was significantly reduced. The results indicate that CBD can effectively inhibit the replication of RNA polymerase of influenza virus H1N1.

CBD inhibits the expression of influenza virus RNA-dependent RNA polymerase, and may inhibit the replication of IAV in host cells and reduce influenza infection. The present invention provides a potential broad-spectrum anti-influenza drug.

EXAMPLE 3: EXPERIMENT OF CANNABIDIOL AGAINST INFLUENZA A VIRUS H5N1

1. Experimental Animals and Preliminary Preparation 6-week-old C57BL/6 male mice, purchased from Beijing Vital River Laboratory Animal Technology Co., Ltd.

The conditions were the same as in Example 1. The animals were routinely raised at the P2 and P3 animal centers (Biosafety levels 2 and 3, P2/P3) of the Institute of Microbiology, Chinese Academy of Sciences. The light cycle was 12 h light/12 h dark, and the animals had free access to food and water. Related experiments were performed after the animals were acclimated to the new environment for 1 day. The China Agricultural University and the Animal Ethics Committee of the State Key Laboratory of Agrobiotechnology (SKLAB-2017-3-002) approved the animal experiments.

The C57BL/6 male mice were randomly divided into 2 groups, 10 mice in each group. From Day 4 after infection, the drug was administered once a day by intraperitoneal injection for 5 consecutive days. The 1000 pfu influenza group was injected with the same amount of normal saline. The specific grouping is as follows:

Influenza group (H5N1 1000 pfu): injected with the same amount of normal saline from Day 4 after infection.

CBD group: administered from Day 4 after infection with H5N1 1000 pfu (cannabidiol, 20 mg/kg/d).

2. Experimental Methods

The amplification method and titer testing method of the H5N1 virus were identical to those in Example 1, except that the virus subtype was H5N1.

The observation and recording of physiological characteristics and onset symptoms of mice were identical to those in Example 1.

From 0 day of post infection (DPI 0) of H5N1 to 11 days of post infection (DPI 10), the mice were weighed daily, and the body weight change percentage was calculated by subtracting the body weight on DPI 0 from the body weight of the day and dividing the difference by the body weight on DPI 0.

The mice infected with H5N1 (infected at a dose of 1000 pfu, and monitored for changes in body temperature), 10 in each group, were subjected to rectal temperature measurement daily on DPI 0 to DPI 12, and the percentage of changes in body temperature was calculated by subtracting the rectal temperature on DPI 0 from the rectal temperature of the day and dividing the difference by the rectal temperature on DPI 0.

On DPI 9 of the challenge, the activity status of the mice was respectively recorded in a video, detected and quantified. Changes in mouse behavior are divided into main actions and grooming actions (standing, sitting, standing up, walking, lying down, head turning, watching, smelling, face washing, etc.). For details, references are made to sections of the experimental materials and methods. Representative behavioral actions within 1 minute were taken, and counting was performed.

The death of H5N1 infected mice was recorded daily.

Figure 13:
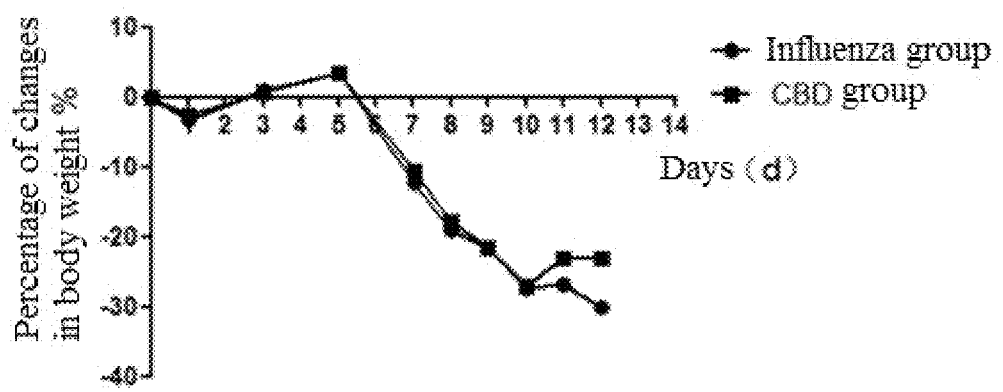
FIG. 13: Changes in body weight of H5N1-infected mice. After the mice were infected with H5N1, the body weight was continuously monitored for 12 days. Data are expressed as mean±standard error (n=10/group).

3. Experimental Results (1) In the CBD Group, the Body Weight Drop Caused by H5N1 Could be Significantly Inhibited As shown in FIG. 13.

As can be seen from the figure, the initial fluctuation of body temperature in mice was due to the stress response that occurred when the mice were purchased for experimentation and acclimated to the new environment. However, since the initial body weight percentage curves of mice in the groups are roughly equivalent, the change caused by the stress response can be ignored. The body weight of the mice began to drop significantly on Day 6 after the infection with influenza virus, reached the lowest point on about Day 10, and then began to rise. However, on Day 12, all the mice died.

Figure 14:
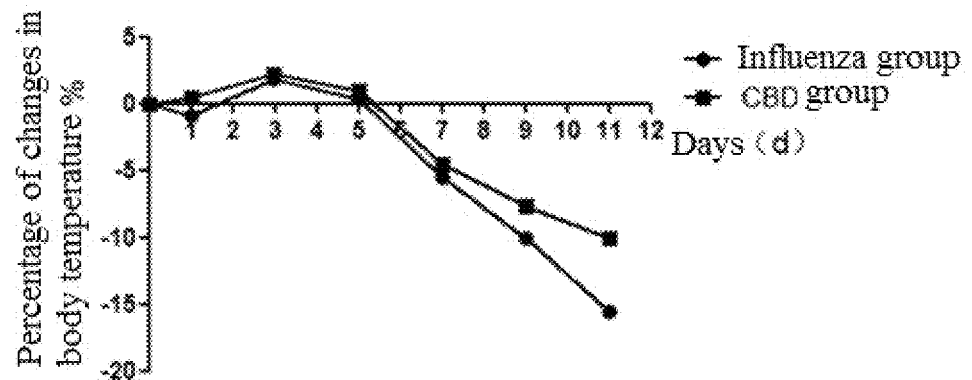
FIG. 14: Changes in body temperature of H5N1-infected mice. After the mice were infected with H5N1, the body temperature was continuously monitored for 11 days. Data are expressed as mean±standard error (n=10/group).

(2) In the CBD Group, the Body Temperature Drop Caused by H5N1 Could be Significantly Inhibited As shown in FIG. 14.

There was a significant difference in changes in body temperature of mice on DPI 9. Compared with the influenza group, in the CBD group (20 mg/kg/d), the body temperature drop could be significantly inhibited. Since half of the mice died on Day 9, statistical analysis could not be performed.

Figure 15:
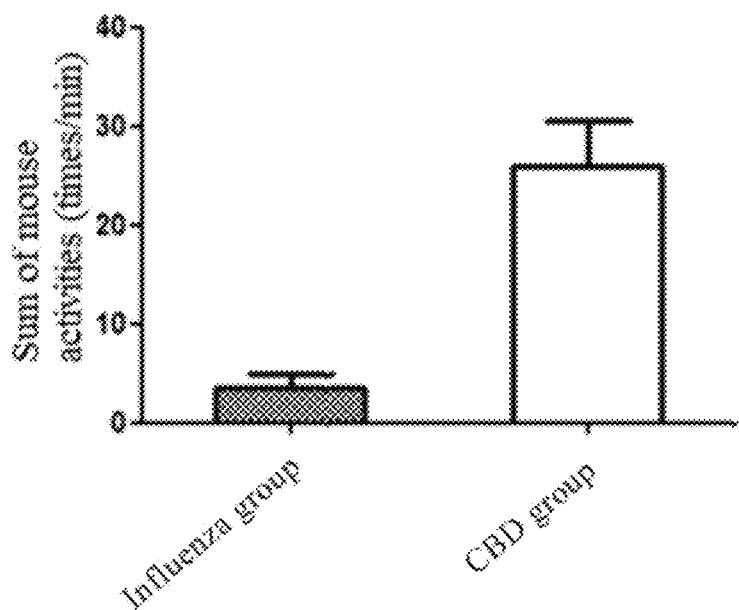
FIG. 15: Changes in behavior of H5N1-infected mice. After the mice were infected with IAV, the behavior on Day 9 was monitored. Data are expressed as mean±standard error (n=5/group). Significance analysis was performed on differences by using a post hoc method, with significant differences expressed as *, ***$p<0.001$.

(3) In the CBD Group, the Influenza Symptoms and Behavioral Discomfort in the H5N1 Infected Group Could be Significantly Reduced As shown in FIG. 15. On DPI 9 (n=5/group), there was a significant difference in changes in behavior of mice (p<0.001). Compared with the influenza group (n=5/group), in the CBD group (20 mg/kg/d) (n=5/group), the activities of the infected mice could be significantly increased, and the discomfort caused by influenza could be significantly alleviated.

Figure 16:
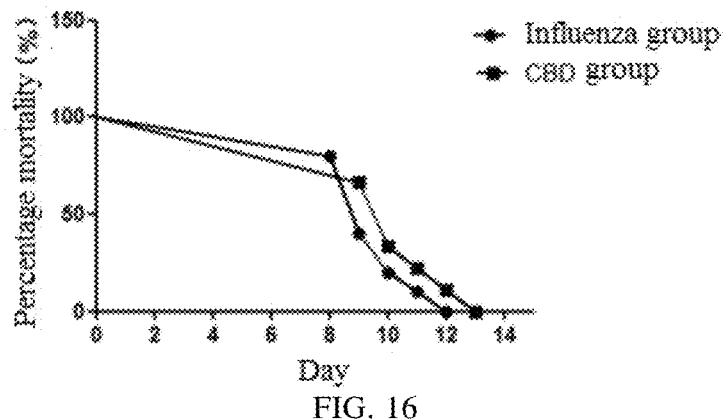
FIG. 16: Mortality of H5N1-infected mice.
Figure 17A:
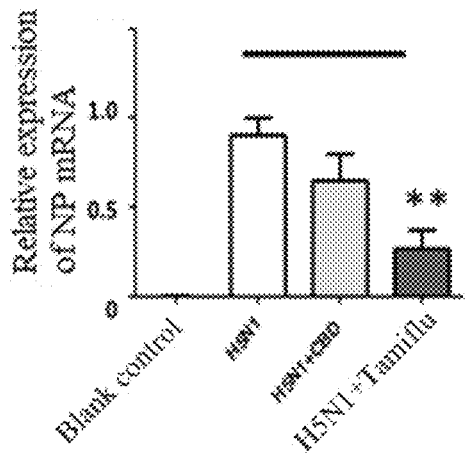
FIG. 17A: Changes in expression of NP gene in a CBD-treated H5N1-infected human lung epithelial cell line A 549. Changes in expression of NP gene in a CBD-treated H5N1-infected human lung epithelial cell line A 549 after 24 h. Data are expressed as mean±standard error, *$p<0.05$.
Figure 17B:
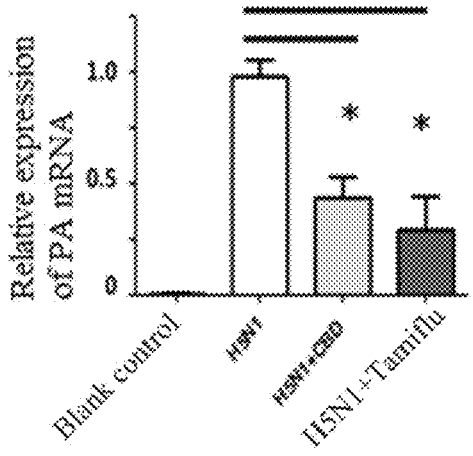
FIG. 17B: Changes in expression of PA gene in a CBD-treated H5N1-infected human lung epithelial cell line A 549. Changes in expression of PA gene in a CBD-treated H5N1-infected human lung epithelial cell line A 549 after 24 h. Data are expressed as mean±standard error, *$p<0.05$.
Figure 17C:
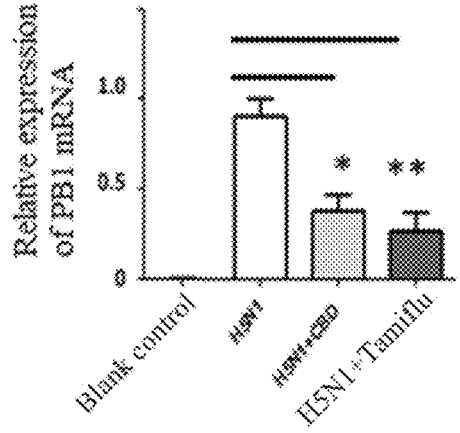
FIG. 17C: Changes in expression of PB1 gene in a CBD-treated H5N1-infected human lung epithelial cell line A 549. Changes in expression of PB1 gene in a CBD-treated H5N1-infected human lung epithelial cell line A 549 after 24 h. Data are expressed as mean±standard error, *$p<0.05$, **$p<0.01$.
Figure 17D:
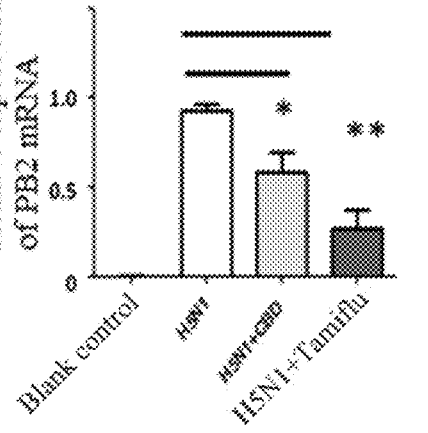
FIG. 17D: Changes in expression of PB2 gene in a CBD-treated H5N1-infected human lung epithelial cell line A 549. Changes in expression of PB2 gene in a CBD-treated H5N1-infected human lung epithelial cell line A 549 after 24 h. Data are expressed as mean±standard error, *$p<0.05$, **$p<0.01$.

(4) In the CBD Group, the Survival Time of the H5N1 Infected Group Could be Significantly Prolonged As shown in FIG. 16. Compared with the influenza group (10/10), there was no significant difference in mortality of the CBD group (10/10). However, in the CBD group (20 mg/kg/d), the survival time of mice after H5N1 infection could be significantly prolonged by 24 hours at each time point (CBD group vs. influenza group, P<0.05).

In addition, since the Kunming mice are a closed colony and C57BL/6s is an inbred line, their sensitivity and response to drugs are different, and at the same time, they are two different lines, which on the other hand illustrates the broad spectrum of CBD.

EXAMPLE 4: IN VITRO EXPERIMENT OF CANNABIDIOL INHIBITING RNA POLYMERASE OF INFLUENZA A VIRUS H5N1

6-well plates were inoculated with a human non-small cell lung cancer cell line A549 (ATCC® CCL-185™), which was divided into the following 4 groups:

control group (high glucose medium DMEM, of which the manufacturer is Sigma and the product code is D5648-1L, diluted to 1 liter with purified water before the experiment), H5N1 infected control group, CBD group (1 μM) and Tamiflu group (1 μM).

The above four groups were cultured overnight at 37° C., and when the cell confluence reached 100% after 18-24 h and there was no gap between cells, the cells were infected with H5N1. At an MOI of 0.01, the cells were infected for 1 h.

The supernatant was sucked and discarded, and the same volume of serum-free medium containing PBS, Tamiflu and CBD was correspondingly added to each group, wherein each serum-free medium contained the same concentration of PBS, Tamiflu and CBD. Incubation was performed in a $CO_2$ incubator at 37° C. for 24 h.

RNA was extracted, and reversely transcribed, and qRT-PCR was used to detect the expression of virus mRNA. RT-PCR primers for detecting expression of NP, PA, PB1 and PB2 genes in H5N1 are as follows:

NP-F1:
(SEQ ID NO: 9)
GTGGCCCATAAGTCCTGCTT

NP-R1:
(SEQ ID NO: 10)
GGTCGCTCTTTCGAAGGGAA

PA-F1:
(SEQ ID NO: 11)
GCCGCAATATGCACACACTT

PA-R1:
(SEQ ID NO: 12)
TTGATTCGCCTCGTTCGTCA

PB1-F1:
(SEQ ID NO: 13)
AGACTACCAGGGCAGACTGT

PB1-R1:
(SEQ ID NO: 14)
CAACTGGCCTCCGATACGAA

PB2-F1:
(SEQ ID NO: 15)
GCAGCAATGGGTCTGAGGAT

PB2-R1:
(SEQ ID NO: 16)
CAATGTTTGGAGGTTGCCCG

The experimental results are shown in FIG. 17A, FIG. 17B, FIG. 17C and FIG. 17D respectively.

The results showed that in the Tamiflu group (1 μM) and the CBD group (1 μM), the expression of NP, PA, PB1 and PB2 genes in H5N1 was significantly reduced. The results indicate that CBD can effectively inhibit the replication of RNA polymerase of influenza virus H5N1.

CBD inhibits the expression of influenza virus RNA-dependent RNA polymerase, and may inhibit the replication of IAV in host cells and reduce influenza infection. The present invention provides a potential broad-spectrum anti-influenza drug.

REFERENCES

Hay, A. J., Gregory, V., Douglas, A. R., and Lin, Y. P. (2001). The evolution of human influenza viruses. Philosophical transactions of the Royal Society of London Series B, Biological sciences 356, 1861-1870.

Bernard, G. R., Luce, J. M., Sprung, C. L., Rinaldo, J. E., Tate, R. M., Sibbald, W. J., Kariman, K., Higgins, S., Bradley, R., Metz, C. A., et al. (1987). High-dose corticosteroids in patients with the adult respiratory distress syndrome. The New England journal of medicine 317, 1565-1570.

Glezen, W. P. (2006). Influenza control. The New England journal of medicine 355, 79-81.

Kolocouris, N., Kolocouris, A., Foscolos, G. B., Fytas, G., Neyts, J., Padalko, E., Balzarini, J., Snoeck, R., Andrei, G., and De Clercq, E. (1996). Synthesis and antiviral activity evaluation of some new aminoadamantane derivatives. 2. J Med Chem 39, 3307-3318.

Ribeiro, A., Almeida, V. I., Costola-de-Souza, C., Ferraz-de-Paula, V., Pinheiro, M. L., Vitoretti, L. B., Gimenes-Junior, J. A., Akamine, A. T., Crippa, J. A., Tavares-de-Lima, W., et al. (2015). Cannabidiol improves lung function and inflammation in mice submitted to LPS-induced acute lung injury. Immunopharmacology and immunotoxicology 37, 35-41.

Although specific embodiments of the present invention have been described in detail, those skilled in the art will appreciate that in light of the teachings of the present invention, various modifications and alterations may be made to those details, and these changes are all within the scope of the present invention. The full scope of the present invention is given by the appended claims and any equivalents thereof.

The invention claimed is:

1. A method of treating influenza or relieving an influenza symptom, comprising a step of administering an effective amount of a product selected from any one of (1) to (3) below to a subject in need:
   (1) cannabidiol or a pharmaceutically acceptable salt or ester thereof;
   (2) a plant extract containing cannabidiol; and
   (3) a pharmaceutical composition, containing an effective amount of cannabidiol or a pharmaceutically acceptable salt or ester thereof, and one or more pharmaceutically acceptable auxiliary materials.

2. The method according to claim 1, wherein the influenza is caused by one or more influenza viruses selected from influenza A virus, influenza B virus, and influenza C virus.

3. The method according to claim 1, wherein the subject is a mammal or a bird.

4. The method according to claim 1, wherein the influenza symptom is at least one selected from the following symptoms caused by influenza:
   fever, cough, headache, muscle pains, and diarrhea.

5. The method according to claim 1, wherein the pharmaceutical composition further comprises an effective amount of one or more ingredients selected from:
   an inosine monophosphate dehydrogenase inhibitor, and an interferon inducer, an M2 ion channel protein inhibitor and a neuraminidase inhibitor.

6. The method according to claim 1, wherein the plant extract containing cannabidiol is a *cannabis* extract containing cannabidiol.

7. The method according to claim 1, wherein the plant extract containing cannabidiol is an industrial *cannabis* extract containing cannabidiol.

* * * * *